US009665933B2

(12) United States Patent
Herrmann et al.

(10) Patent No.: US 9,665,933 B2
(45) Date of Patent: May 30, 2017

(54) METHOD AND APPARATUS FOR INSPECTING CONTAINERS, SUCH AS BOTTLES OR SIMILAR CONTAINERS (71) Applicants: Jürgen Herrmann, Rosenheim (DE); Wolfgang Schorn, Hönningen (DE); Marius Michael Herrmann, Rosenheim (DE); Xiang Zhang, Wetter (DE)

(72) Inventors: Jürgen Herrmann, Rosenheim (DE); Wolfgang Schorn, Hönningen (DE); Marius Michael Herrmann, Rosenheim (DE); Xiang Zhang, Wetter (DE)

(73) Assignee: KHS GmbH, Dortmund (DE)

( * ) Notice: Subject to any disclaimer, the term of this patent is extended or adjusted under 35 U.S.C. 154(b) by 159 days.

(21) Appl. No.: 14/542,871

(22) Filed: Nov. 17, 2014

(65) Prior Publication Data
US 2015/0071523 A1 Mar. 12, 2015

Related U.S. Application Data (63) Continuation-in-part of application No. PCT/EP2013/001092, filed on Apr. 13, 2013.

(30) Foreign Application Priority Data

May 18, 2012 (DE) .................. 10 2012 009 783

(51) Int. Cl.
*G06K 9/20* (2006.01)
*G06T 7/00* (2017.01)
*G01N 21/90* (2006.01)

(52) U.S. Cl.
CPC .......... *G06T 7/0008* (2013.01); *G01N 21/90* (2013.01); *G01N 21/9036* (2013.01);
(Continued)

(58) Field of Classification Search
None
See application file for complete search history.

(56) References Cited

U.S. PATENT DOCUMENTS 5,729,340 A 3/1998 Griesbeck et al.

FOREIGN PATENT DOCUMENTS

DE 3611536 10/1987
DE EP 1628241 A1 * 2/2006 ............. B65C 9/067
(Continued)

OTHER PUBLICATIONS

International Preliminary Report on Patentability of PCT/EP2013/001092, dated Nov. 27, 2014, and English translation thereof.
(Continued)

*Primary Examiner* — Siamak Harandi
*Assistant Examiner* — Mai Tran
(74) *Attorney, Agent, or Firm* — Nils H. Ljungman & Associates (57) ABSTRACT A method and apparatus for inspecting containers, such as bottles or similar containers. The abstract of the disclosure is submitted herewith as required by 37 C.F.R. §1.72(b). As stated in 37 C.F.R. §1.72(b): A brief abstract of the technical disclosure in the specification must commence on a separate sheet, preferably following the claims, under the heading "Abstract of the Disclosure." The purpose of the abstract is to enable the Patent and Trademark Office and the public generally to determine quickly from a cursory inspection the nature and gist of the technical disclosure. The abstract shall not be used for interpreting the scope of the claims. Therefore, any statements made relating to the abstract are not intended to limit the claims in any manner and should not be interpreted as limiting the claims in any manner.

20 Claims, 6 Drawing Sheets (52) U.S. Cl.
CPC ....... *G01N 21/9045* (2013.01); *G06K 9/2054* (2013.01); *G06T 7/004* (2013.01); *G06T 2207/30108* (2013.01)

(56) References Cited

FOREIGN PATENT DOCUMENTS

| | | |
|---|---|---|
| DE | 102008053876 | 5/2010 |
| DE | 102010032166 | 1/2012 |
| EP | 1628241 | 2/2006 |
| JP | H 04128635 A | 4/1992 |
| JP | H 04265847 A | 9/1992 |
| JP | H 0599861 A | 4/1993 |
| JP | 2005 119706 A | 5/2005 |
| JP | 2005 345423 A | 12/2005 |

OTHER PUBLICATIONS

International Search Report of PCT/EP2013/001092, dated Aug. 8, 2013, and English translation thereof.

\* cited by examiner

METHOD AND APPARATUS FOR INSPECTING CONTAINERS, SUCH AS BOTTLES OR SIMILAR CONTAINERS

CONTINUING APPLICATION DATA

This application is a Continuation-In-Part application of International Patent Application No. PCT/2013/001092, filed on Apr. 13, 2013, which claims priority from Federal Republic of Germany Patent Application No. 10 2012 009 783.2, filed on May 18, 2012. International Patent Application No. PCT/2013/001092 was pending as of the filing date of this application. The United States was an elected state in International Patent Application No. PCT/2013/001092.

BACKGROUND

1. Technical Field

The present application concerns a method for inspecting at least one container, such as a bottle, by detecting a position of a feature arranged on a surface of the container. Furthermore the present application concerns a corresponding apparatus or corresponding container inspector.

2. Background Information

Background information is for informational purposes only and does not necessarily admit that subsequently mentioned information and publications are prior art.

In the context of the present description, a container or bottle comprises any type of container which can be filled with bulk product. An empty container or empty bottle refers to a container or bottle which has not yet been filled with bulk product. Such containers can for example be used as bottles for fluids, for example drinks. The containers, e.g. bottles, can be made of a transparent or translucent material, e.g. glass, or a translucent plastic such as PET. It is also conceivable that the containers comprise other materials and can be filled with other products. Before such containers are filled and before they pass through a labeling machine, or after they have passed through such a labeling machine, these containers are thoroughly inspected with suitable inspection devices. For example it is provided to carry out a foreign body inspection in which the containers are inspected for undesirable foreign bodies in their interior.

Usually, to identify their type or the product to be contained, containers, such as bottles, are marked with specific features on their surface, such as an embossing or relief or specific labels. To be able to essentially guarantee that on inspection of the containers, usually bottles, these features located on the surface are not detected as faults, i.e., as supposedly foreign bodies, it is necessary and/or desired to take suitable measures here in order, despite the presence of labels or embossing, to be able to carry out a reliable inspection of the bottles with regard to actual defects or the presence of dirt particles.

OBJECT OR OBJECTS

In this context, an object of the present application is to provide a method and a corresponding apparatus for inspection of at least one container or bottle, which essentially guarantees that the inspection can be carried out reliably and securely without an excessive number of misdetections. This means that it is desirable for such an inspection to be able to be carried out on such containers or bottles efficiently but with a minimum safety loss for example on an illumination check.

SUMMARY

To achieve this object, according to the present application a method is proposed for inspection of at least one bottle according to the present application, and an apparatus for inspection of at least one bottle according to the present application.

According to the present application, a method is provided for inspection of at least one bottle with detection of a position of a feature arranged on a surface of the bottle. Before inspection, the bottle passes through a detection module in which a predefined position of the feature to be detected is scanned optically and/or by sensors to detect an actual position of the feature, and the actual position is determined and provided.

A feature such as an embossing, décor seam or production seam is normally detected by means of an illumination process which, because of the lower light intensity and/or targeted reflection at the container surface, allows the detection of concrete structures and/or shapes.

In a subsequent first inspection then a mask is generated for the determined position of the feature, so that no fault is detected in the region of the mask on performance of the first inspection. This fault inspection is normally performed as a light transmission process in order to detect substances, defects and faults in the wall or interior of a container. Compared with a light reflection inspection, a much higher lux figure or illumination intensity is selected, at which said feature e.g. the embossing would be flashed over, i.e. could not be detected as a separate structure or in its precise or general position and extension.

According to one possible embodiment, the mask is an area or zone on the surface of the bottle that can be essentially excluded from consideration and/or inspection for defects, cracks, dirt, etc. This exclusion zone or safe zone or exclusion area covers the container feature or container surface feature, such as an embossment, raised decoration, impression, bottle seam, or other such container feature that is part of the bottle or container, as well as extends beyond the container feature to cover an area surrounding the container feature. In other words, the exclusion zone covers an area that is large enough to encompass the entire container feature, but is not substantially larger than the container feature to avoid encompassing adjacent defects and/or dirt. Anything within the exclusion zone that is detected is therefore considered to be an acceptable part of the container. The exclusion zone should encompass or surround the container feature, i.e., the container feature should be located in the exclusion zone, so that when the container is inspected, the container feature is not considered to be a defect or other erroneous portion of the container, and thus the container will pass the inspection process and be moved on for further handling in the container handling system.

After performance of the first inspection, the bottle is rotated by a predefined angle, wherein the position of the feature is calculated with the offset generated by rotation and provided as a new position for performance of a second inspection. On the second inspection, a second mask is generated for the new position of the feature provided, so that no fault is detected in the region of the second mask on performance of the second inspection, wherein if the bottle is not rotated essentially precisely, the feature is not in the region of the second mask and consequently is detected as a fault. When a fault is detected, the bottle is ejected from the corresponding system and where applicable examined more closely or subjected to a repeat inspection.

In a possible embodiment of the method according to the present application, the predefined angle is selected as a 90 degree angle.

According to at least one possible embodiment, the rotation of the container or bottle between a first inspection and a second inspection is performed in order to permit the detection of defects in the container that may not have been detected in the first inspection. For example, it is possible that some defects, such as cracks or scratches in the container wall, may not be detectable or perceptible by the first detection apparatus, such as a camera, from certain angles or directions. By rotating the container, the defect can be inspected by the second detection apparatus from a different angle or viewpoint than the first apparatus, and thus the previously undetectable defect might now be detected. Virtually any degree of rotation can be utilized to essentially change the "point of view" of the second detection apparatus with respect to the defect, although larger degrees of rotation, such as within the range of 60 to 120 degrees, will be more likely than smaller angles to permit a much different view of the defect to increase the chances of detection.

In a further embodiment of the method according to the present application, the predefined position of the feature to be detected is scanned optically and/or by sensors with a 360 degree cover to detect the actual position of the feature. For this in the detection module provided, an arrangement for example of four cameras is proposed which stand at an angle of 90 degree to each other and thus can scan the bottle over the full periphery as it passes through the detection module. The term "camera" is not restrictive here. Rather the term "camera" includes all or substantially all suitable image or inspection recording devices. Furthermore in the detection module, to scan the bottle with the cameras provided, illumination units are provided, the arrangement and type of which are in one possible embodiment selected depending on the type of feature.

The term "position" in the context of the present description means an angular position and a height position of the feature in relation to the system through which the bottle passes. The passage of the bottle through the detection module and on through the system for inspection is normally achieved by so-called belt conveyors or belt-like transporters. After passing through the detection module, the bottle to be inspected is supplied to an inlet of a container inspector for side wall inspection. Then for the position of the feature determined, in the container inspector a mask is produced for the inspection region concerned in the respective side wall inspection, so that in the region of the mask, no fault or dirt detection is carried out. After performance of the side wall inspection at the inlet of the container inspector, during its passage the bottle is rotated by a belt drive through an angle as close to 90 degree as possible, as already stated. The position of the feature is then calculated by the offset generated by rotation and transmitted as a new position of the feature to the side wall inspection at an outlet of the container inspector, as an input value. Using this determined new position, a further mask is generated so that at the outlet from the side wall inspection too, no misdetection occurs in the region of the mask. If however the bottle is not rotated sufficiently precisely, despite masking, the feature will not be in the region of the mask and will consequently be detected as a side wall fault.

As already stated, in an embodiment of the method according to the present application, the first inspection corresponds to a side wall inspection at an inlet to the container inspector, and the second inspection to a side wall inspection at an outlet of the container inspector. It is also conceivable, as already stated, that the bottle is rotated on passage by a belt drive of a container inspector.

In a further embodiment of the method according to the present application, after rotation of the bottle by a predefined angle, e.g. 90 degree, before the second inspection the bottle is supplied to a second detection module in which the new position of the feature to be detected is scanned optically and/or by sensors, in one possible embodiment with a 360 degree coverage, to detect the actual new position of the feature, and the actual new position is determined and provided.

Then on the subsequent second inspection, a mask is generated for the actual new determined position of the feature, so that no fault is detected in the region of the mask on performance of the second inspection. This essentially guarantees that misdetection due to defective masking of the feature based on faulty rotation is essentially avoided, since after rotation a repeat detection of the actual new position is carried out. If the bottle has been rotated incorrectly, this fault can virtually be compensated by the second detection module or the detection performed therein of the actual new position. Thus no bottles, or at least fewer bottles, are ejected which have no contamination, but were detected as faulty on the second inspection because of faulty masking of the feature. With this embodiment of the method according to the present application, the safety can be increased further on a light transmission test of a bottle.

In a further embodiment of the method according to the present application, the actual determined position before the first inspection and the actual new determined position before the second inspection are compared and from this an actual rotation angle determined. In this way the rotation or the unit performing the rotation can be monitored and adjusted accordingly. If this is not possible, in all or substantially all or most or some cases, no bottles will be ejected in error because of this faulty rotation.

In a further embodiment of the method according to the present application, the actual determined rotation angle is used to monitor a rotation angle and compared with the predefined angle and its tolerances, wherein a deviation outside the tolerances is detected as a fault, because of which the unit performing the rotation must be changed or should be changed or at least readjusted.

According to a further embodiment of the method according to the present application, in the detection unit, different illumination units are provided which are selected according to the type of feature to be detected.

The present application furthermore concerns an apparatus for fault inspection (referred to below as simply inspection) of at least one bottle with detection of a position of a feature arranged on a surface of the bottle. The apparatus according to the present application comprises at least one detection module which is designed to scan a predefined position of a feature to be detected optically and/or by sensors in order to detect an actual position of the feature, and to determine and provide the actual position. Furthermore the apparatus according to the present application comprises a first inspection unit which is designed, on the basis of a determined position of the feature, to generate a mask and furthermore perform an inspection, wherein no misdetection occurs in the region of the mask on performance of the inspection.

This means that the data processing for determining the feature extent and position, and the dynamic mask adaptation, can also be carried out in one or more control and computing units which need not necessarily be part of the inspection unit.

Furthermore the present apparatus according to the present application comprises a rotary module which is designed to rotate the bottle by a predefined angle after a first inspection and to calculate the position of the feature with an offset generated by the rotation, and provide this as a new position for performance of a second inspection, wherein in the same way, no misdetection occurs in the region of the second mask. This apparatus is functionally connected in the known manner with an ejection module which ejects contaminated or damaged containers from the stream.

An embodiment of the present apparatus furthermore comprises one or more further detection modules which are arranged after the first inspection unit and after the rotary module, and designed to scan the new position of the feature to be detected optically and/or by sensors to detect the actual new position, in order to determine the actual new position and transmit this to the second inspection unit, so that on a subsequent second inspection, the second inspection unit generates a mask for the actual new determined position of the feature, so that no fault is detected in the region of the mask on performance of the second inspection.

The planar or spatial extent of the feature is dependent on the rotation and transport process of the container, since the shadow area of the feature relative to the inspection camera is relevant. Thus the discrete parts of a feature on the back of the container can be determined and then excluded by means of masking, but on a light transmission inspection would nonetheless be detected as faults. The back is here the container surface or side which is facing away from the camera or sensor element.

Therefore by means of the control and computing unit, the data on the planar and/or spatial extent of the one or more features are generated and transmitted for dynamic adaptation of the position and the planar and/or spatial extent of the mask concerned.

Thus the control and computing unit essentially ensures or promotes that as small of a region of the container as possible is excluded from inspection.

The mask is here in one embodiment dimensioned such that this corresponds to the area of the marking or extends beyond the marking by an area which corresponds to the resolution of the sensors, in one possible embodiment of a camera.

Different illumination units can be provided in both the first and second detection modules, which are selected according to the type of feature to be detected. It is furthermore conceivable that in both the first and in the second detection modules, four cameras are arranged at an angular spacing of 90 degrees to each other, so that a 360 degree coverage is achieved on scanning of the bottle. As already stated initially, the term "camera" is not restrictive here but rather more includes all or substantially all or most or some suitable image or inspection recording devices. Both the first and the second inspection unit each comprise corresponding illumination and image recording devices or sensor systems, in order to be able to carry out a suitable inspection, in one possible embodiment a side wall inspection of the bottles passing through. Usually a belt drive is provided for bottle rotation between the two inspection units, which lies on the path of the corresponding bottle from the first inspection unit to the second inspection unit, wherein naturally other systems are also known, for example for fixing and rotating a container at its mouth.

In at least one possible embodiment, the inspection method involves inspecting empty containers or empty bottles prior to filling with a product. Such empty containers or empty bottles may be made of a transparent and/or translucent material, such as glass, plastic, PET, or similar material. The inspection apparatus may be arranged such that the containers or bottles pass between a light source and a camera or similar detection apparatus. In this embodiment, the light passes through the container or bottle and then travels to the camera or similar detection apparatus. In another possible embodiment, both the light source and the camera or similar detection apparatus are on the same side of the container or bottle. In this embodiment, the light reflects off the outer surface of the container or bottle to the camera or similar detection apparatus.

The apparatus according to the present application may be suitable for executing a method according to the present application as described above.

Further embodiments of the present application arise from the description and enclosed drawings.

Evidently the features cited above and to be explained below can be applied in the combination given and also in other combinations or alone, without leaving the limits of the present application.

The above-discussed embodiments of the present invention will be described further herein below. When the word "invention" or "embodiment of the invention" is used in this specification, the word "invention" or "embodiment of the invention" includes "inventions" or "embodiments of the invention", that is the plural of "invention" or "embodiment of the invention". By stating "invention" or "embodiment of the invention", the Applicant does not in any way admit that the present application does not include more than one patentably and non-obviously distinct invention, and maintains that this application may include more than one patentably and non-obviously distinct invention. The Applicant hereby asserts that the disclosure of this application may include more than one invention, and, in the event that there is more than one invention, that these inventions may be patentable and non-obvious one with respect to the other.

DESCRIPTION OF EMBODIMENT OR EMBODIMENTS

Figure 1:
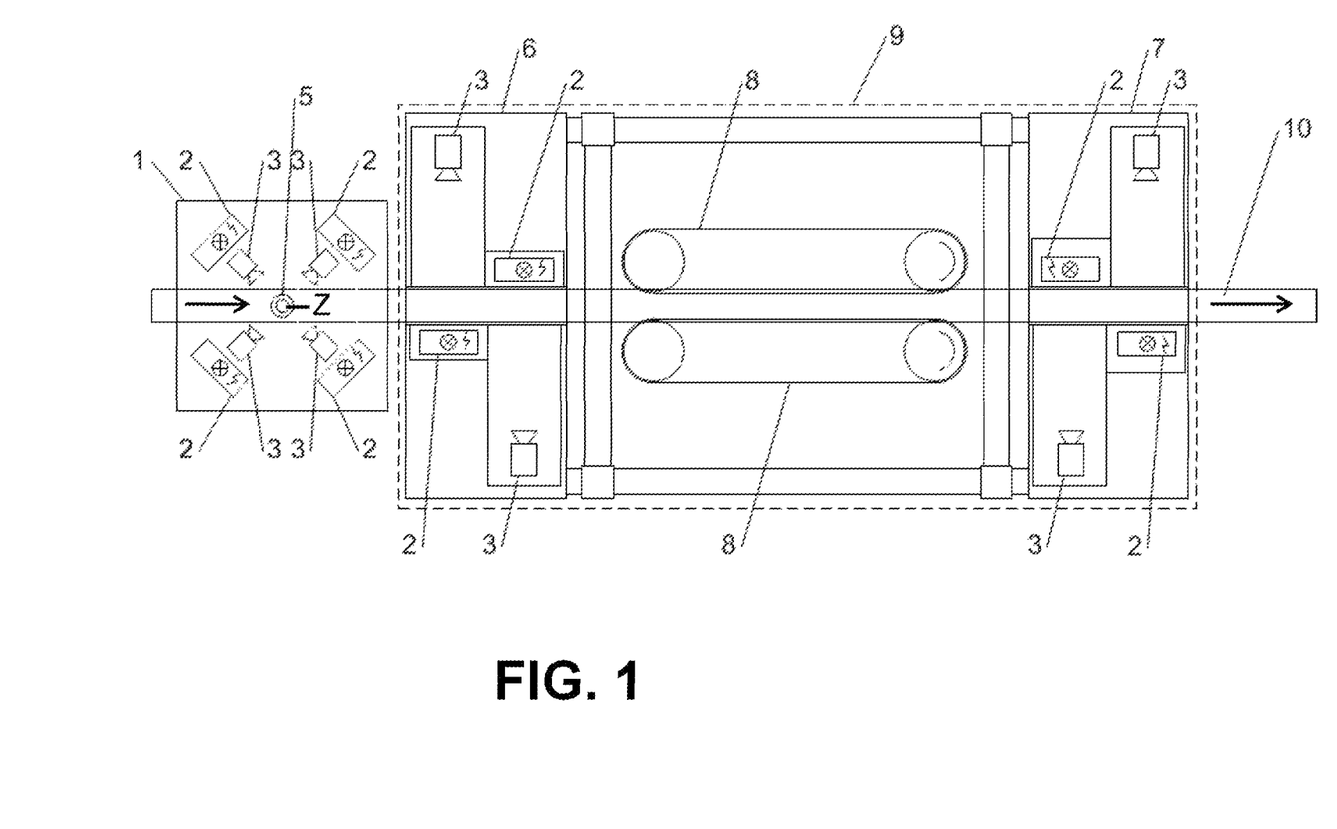
FIG. 1 shows diagrammatically a top view of a first embodiment of an apparatus according to the present application for inspecting at least one bottle.

FIG. 1 shows a top view of an apparatus according to the present application for inspecting at least one bottle with detection of a position of a feature arranged on a surface of the bottle. The apparatus shown here comprises a first detection module 1 followed by a container inspector 9. A bottle to be inspected passes in direction 10 first through the first detection module 1 and then through the container inspector 9. The first detection module 1 in the form shown here comprises four illumination units 2 and four image recording units or sensor systems 3. The illumination units 2 are each arranged after the respective image recording unit 3, so that an illumination unit 2 and a respective image recording unit 3 lie in a line and the resulting four lines of the four illumination units 2 and the corresponding four imaging units 3 meet in a center Z. The illumination units 2 below each other, and the imaging units 3 below each other, are here arranged at an angle of 90 degrees to each other. If the at least one bottle 5 is situated in the center or intersection Z of said lines, this bottle 5 can be examined or scanned precisely or essentially precisely or generally by the illumination units 2 and the image recording units 3, so that an actual position of the feature can be detected and hence determined and provided. The actual position of the feature is detected in a predefined region of the surface of the bottle in which the feature is arranged according to the definition. In at least one possible embodiment, this means that the bottle is not scanned over its entire height by the illumination units 2 and image recording units 3, but the region which is scanned is restricted in advance to a predefined position of the feature to be detected.

If now the actual position of the feature is detected and hence determined, this actual determined position is transmitted to an inlet 6 of the subsequent container inspector 9. The control and computing unit known for this is not shown but can be provided as a central control and computer unit, or decentrally e.g. integrated in the inspection units.

The inlet 6 of the container inspector 9 corresponds here to a first inspection unit and comprises side wall inspection modules for performance of a side wall inspection of a bottle or container passing through the inlet 6 of the container inspector 9. In the embodiment shown here, first an image recording unit 3 and then an illumination unit 2 are provided, wherein in each case an image recording unit 3 and an illumination unit 2 lie opposite each other, and a bottle passing through the inlet 6 runs precisely or essentially precisely or generally between the illumination unit 2 and the image recording unit 3. In the embodiment shown here, the assembly of an image recording unit 3 and an illumination unit 2 is provided twice in succession, in a mutually complementary configuration. Using the actual determined position of the feature, a mask is generated in the inlet 6 of the container inspector 9, so that on performance of the first inspection for detection of faults or dirt, no misdetection occurs in the region of the mask. This means that the feature is itself excluded from fault detection, which prevents or restricts or minimizes the desired feature on the surface of the bottle being perceived for example as dirt.

By means of the control and computing unit, the data on the planar and/or spatial extension of the one or more features, which are dependent on the rotary and transport process of the container, are used for dynamic adaptation of the position and the planar and/or spatial extent of the respective masks. By means of the control and computing unit it is now essentially ensured or promoted that as small a region as possible is excluded from inspection.

The mask is possibly dimensioned so that this protrudes beyond the marking by an area which corresponds to the resolution of the sensors, in one possible embodiment of the camera.

After performance of the first inspection, the bottle is rotated through a predefined angle by a belt drive 8 of the container inspector 9. This is usually an angle of 90 degrees. After performing the rotation, the bottle 5 reaches an outlet 7 of the container inspector 9. The outlet 7 is designed correspondingly to inlet 6 but as a mirror image, and corresponds here to a second inspection unit. Here too, the bottle passes at least once and usually twice through a combination of illumination unit 2 and image recording unit 3. Here the assembly of illumination unit 2 and image recording unit 3 is again punctually symmetrical to a center point arranged centrally on the belt. The actual determined position of the feature is calculated with the offset generated by the rotation and transmitted as a new position and extension of the feature to the side wall inspection at outlet 7 of the container inspector 9 as an input value. The side wall inspections at outlet 7 thus determine the position of the feature for the bottle, and proceed in the same manner as the side wall inspection modules at inlet 6 in relation to masking and adaptation of fault detection.

Containers detected as defective are ejected downstream in the known manner.

Figure 2:
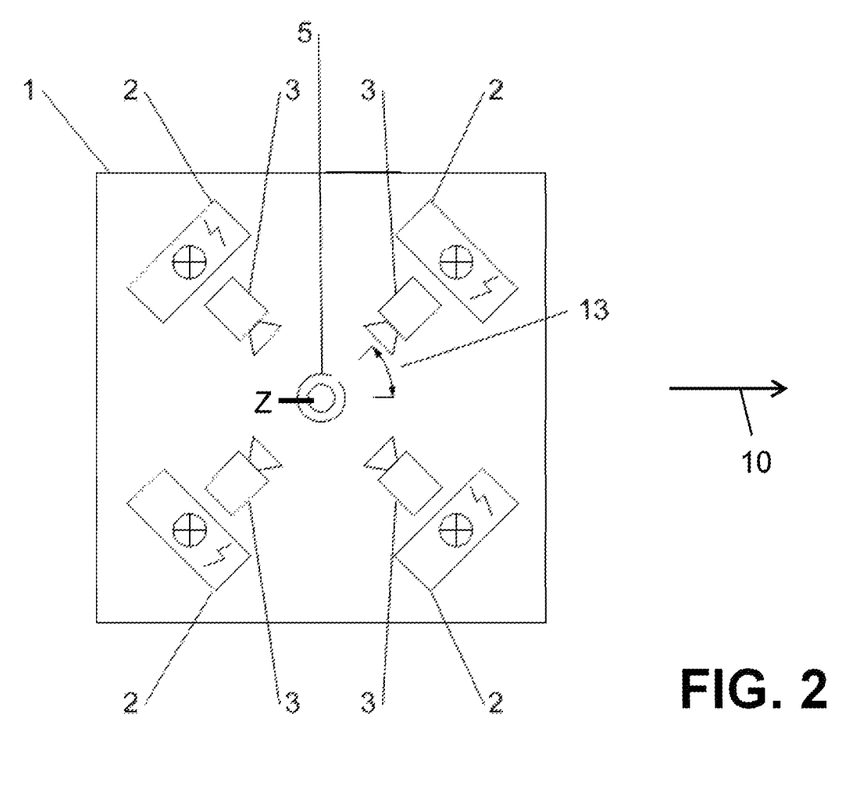
FIG. 2 shows diagrammatically a top view of an embodiment of a detection module, as provided in the embodiment of the apparatus according to the present application shown in FIG. 1.

FIG. 2 shows a top view of a detection module 1, as provided in the embodiment of FIG. 1. Four image recording units 3 and four illumination units 2 associated with the image recording units 3 are shown. In relation to a center point Z, the illumination units 2 each lie behind the image recording units 3, and with their associated image recording units 3 lie on a line, wherein the resulting four lines intersect precisely or essentially precisely or generally at the center point Z. If now a bottle 5 is situated precisely or essentially precisely or generally at this center point Z, optimum scanning of the bottle 5 by the illumination and image recording units is possible. In the case shown here, the illumination units 2 and associated image recording units 3 are arranged offset to each other by an angle of 90 degrees. This allows an optimum 360-degree scanning of a predefined region on a surface of a bottle 5 passing through the detection module. Also the illumination units 2 and image recording units 3 are arranged at an angle 13 of around 45 degrees in relation to a passage direction 10. The illuminations or illumination units 2 can be selected according to the type of feature to be detected on the surface of a bottle passing through the detection module. Also the position of the illumination units 2 can be selected according to the type of feature on the surface of a bottle passing through the detection unit.

Figure 3:
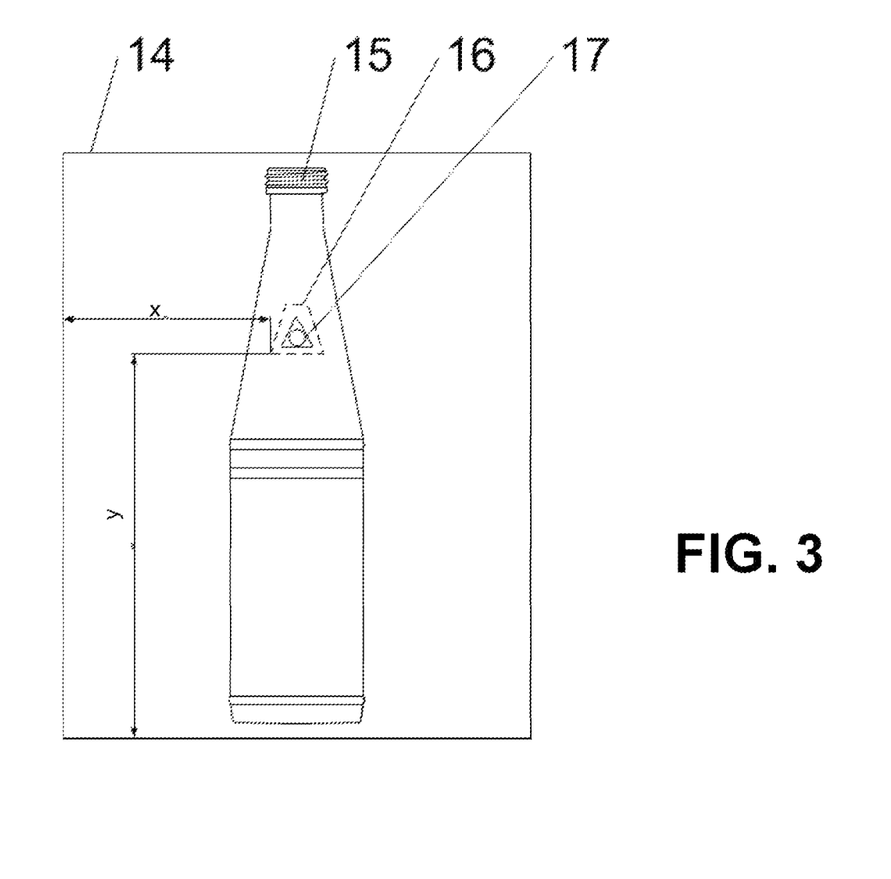
FIG. 3 shows as an example, in diagrammatic depiction, a bottle with a mask correctly positioned in relation to a feature.

FIG. 3 shows an example image of a bottle with a mask correctly positioned in relation to a feature. The image 14 shows a bottle 15 with an object or feature 17 and a generated mask 16 for performance of an inspection. The object 17 or feature 17 is the feature on the surface of the bottle 15 which is to be detected and provided with a mask 16 in advance of an inspection, to prevent or restrict or minimize the feature 17 being interpreted as a fault on inspection.

Figure 4:
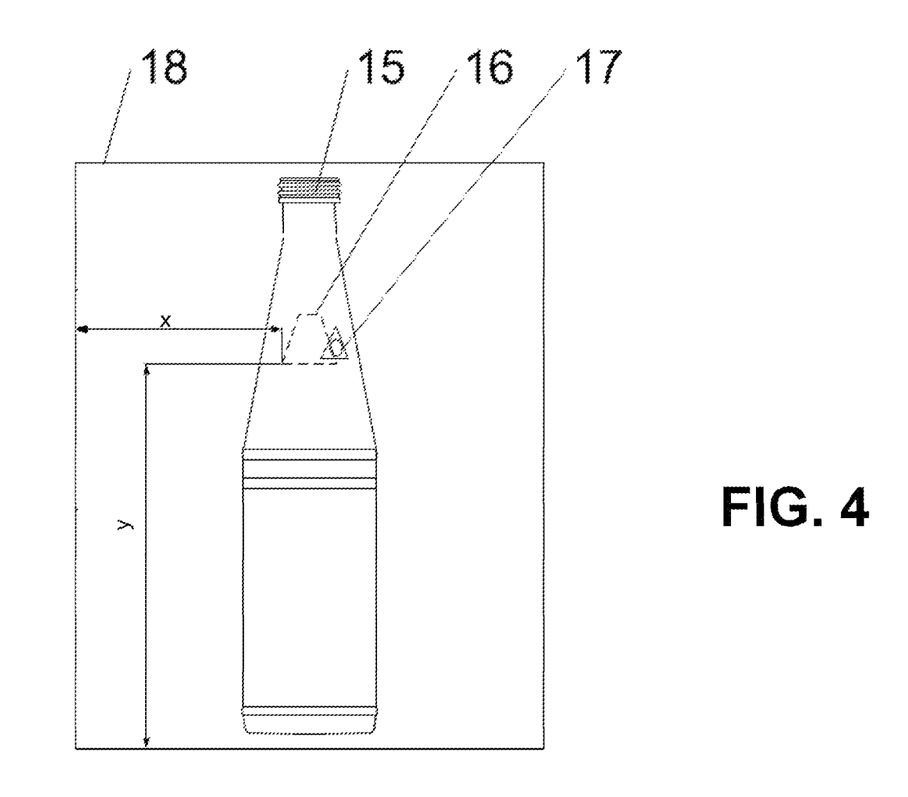
FIG. 4 shows diagrammatically in comparison a bottle with a mask incorrectly positioned in relation to a feature.

FIG. 4 in contrast shows a example image 18 of a bottle 15 with a feature 17, wherein here the mask 16 which is to be formed on the feature 17 in advance of an inspection is not correctly positioned, which may be the result of a faulty rotation of the bottle before performance of a second inspection. The position of the feature 17 is given by coordinates x and y in both FIG. 3 and FIG. 4. Y indicates the height position and x describes an angular position of feature 17 on a corresponding periphery of the bottle 15.

Figure 5:
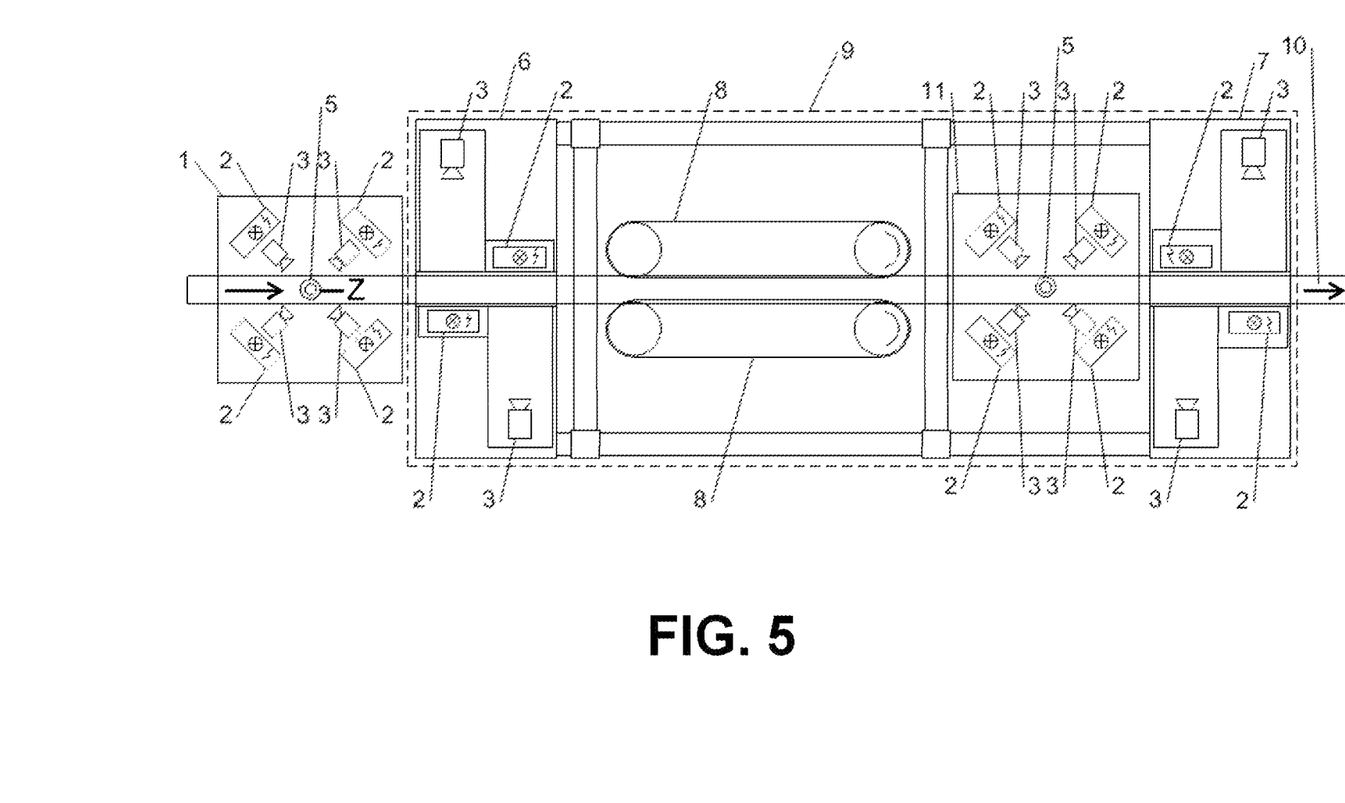
FIG. 5 shows diagrammatically a top view of a second embodiment of an apparatus according to the present application, with a first and a second detection module.

FIG. 5 shows diagrammatically a top view of a second embodiment of the apparatus according to the present application for performance of an inspection of at least one bottle. In contrast to the embodiment in FIG. 1, the embodiment shown here has a second detection module 11 connected upstream of a second inspection at the outlet 7 of the container inspector 9. This means that a bottle 5, passing in the passage direction 10 through the embodiment of the apparatus according to the present application, first passes a first detection module 9 then an inlet 6 of the container inspector, then a belt drive 8, then a second detection module 11, and finally an outlet 7 of the container inspector 9. The second detection module 11 is constructed similarly to the first detection module 1 and, after passage of a bottle 5 through the belt drive 8 and corresponding rotation of the bottle 5 by the belt drive 8, essentially ensures or promotes that the position of the feature is not simply calculated with the rotation performed or a corresponding offset included and from this a new position determined for the second inspection at the outlet 7, but rather that the new position of the feature is determined afresh before passage through the second inspection at the outlet 7. The new position of the feature is determined in the same way as the actual position of the feature was determined in the first detection module. The angular position and height position of the feature determined from this are transmitted to the subsequent side wall inspections at the outlet 7 of the container inspector 9. These inspection systems use a mask for the new determined position of the feature, i.e. a second mask, in the inspection region concerned of the respective side inspection, so that in the region of the second mask—as previously in the region of the first mask on passage through the first inspection—no fault detection for dirt is carried out. If the rotation of the bottle by the belt drive 8 is not sufficiently precise, the feature will nonetheless be masked at the correct position by the second detection module 11.

The principle of determining the extent of the feature on the container or bottle, transmission of the data and the resulting dynamic adaptation of the position and the planar or spatial extent of one or more masks, is the same for the embodiments described.

Depending on inspection task, it may naturally be useful and sufficient for one inspection device to be provided, or one inspection step to be performed, with said dynamic masking.

Figure 6:
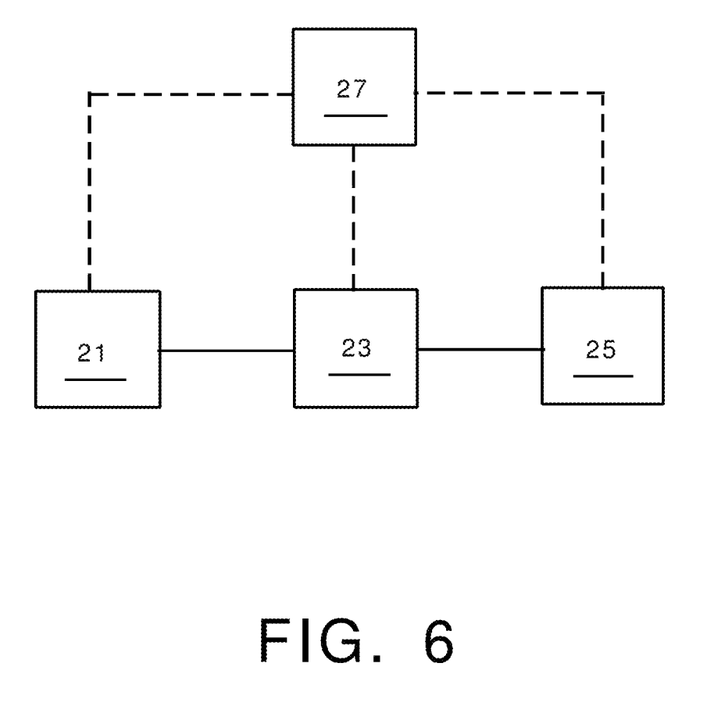
FIG. 6 shows a box diagram of a container inspection arrangement and associated devices according to at least one possible embodiment.

FIG. 6 shows a box diagram of a container inspection arrangement and associated devices according to at least one possible embodiment. The container inspection arrangement includes a container detection arrangement 21, a container inspection arrangement 23, a container ejection arrangement 25, and a control arrangement 27. The container ejection arrangement 25 is designed to eject containers from the stream of containers, which ejected containers have a defect or are in some other type of unacceptable condition. Each of the container detection arrangement 21, the container inspection arrangement 23, and the container ejection arrangement 25 are operatively connected to the control arrangement 27. The control arrangement 27 is an electronic or computer control arrangement 27 that coordinates the functions and operations of the different portions of the container inspection arrangement. For example, when a defective or unacceptable container is detected by the container inspection arrangement 23, the inspection information is sent to the control arrangement 27. The control arrangement 27 then controls the container ejection arrangement 25 to cause the ejection of the defective or unacceptable container out of the stream of containers. Other functions and operations of the different portions of the container inspection arrangement can be similarly controlled and/or coordinated by the control arrangement 27, either automatically or by manual control by a user.

One feature or aspect of an embodiment is believed at the time of the filing of this patent application to possibly reside broadly in a method for fault inspection of at least one container, in one possible embodiment of the present application bottles of glass, PET or another transparent material, with detection of a position of at least one feature arranged on a surface of the container, such as for example an embossing, a décor seam or similar, wherein before the fault inspection by means of at least one inspection module, the container passes through a detection module in which a predefined position of the feature to be detected is scanned optically and/or by sensors to detect an actual position of the feature and the actual position is determined, in a subsequent first inspection at the at least one inspection unit, a first mask is generated for the determined position of the feature so that no misdetection occurs in the region of the first mask on performance of the first inspection, after performance of the first inspection the container is rotated by a predefined angle, a second inspection takes place wherein during the further inspection, a further mask is generated for the provided new position of the feature, so that no misdetection occurs in the region of the second mask on performance of the second inspection, wherein if the container is not rotated essentially precisely, the feature is not in the region of the second mask and is detected as a fault, wherein the position of the feature and its planar extension is calculated with the offset generated by rotation and serves as a new position and extension of the respective masks.

Another feature or aspect of an embodiment is believed at the time of the filing of this patent application to possibly reside broadly in the method, wherein the predefined angle is selected at an angle of 90 degrees.

Yet another feature or aspect of an embodiment is believed at the time of the filing of this patent application to possibly reside broadly in the method, wherein the predefined position of the feature to be detected is scanned optically and/or by sensors with a 360 degrees coverage to detect the actual position of the feature.

Still another feature or aspect of an embodiment is believed at the time of the filing of this patent application to possibly reside broadly in the method, wherein the first inspection constitutes a side wall inspection in an inlet to a container inspector.

A further feature or aspect of an embodiment is believed at the time of the filing of this patent application to possibly reside broadly in the method, wherein the second inspection constitutes a side wall inspection in an outlet of a container inspector.

Another feature or aspect of an embodiment is believed at the time of the filing of this patent application to possibly reside broadly in the method, wherein the container is rotated, on passage of the container, by a belt drive of a container inspector.

Yet another feature or aspect of an embodiment is believed at the time of the filing of this patent application to possibly reside broadly in the method, wherein after rotation of the container by a predefined angle, before the second inspection the container passes through a second detection module in which the new position of the feature to be detected is scanned optically and/or by sensors to detect the actual new position of the feature and the actual new position is determined, in the subsequent second inspection the second mask is generated for the actual new determined position of the feature, so that no misdetection occurs in the region of the second mask on performance of the second inspection.

Still another feature or aspect of an embodiment is believed at the time of the filing of this patent application to possibly reside broadly in the method, wherein the actual determined position before the first inspection and the actual new determined position before the second inspection are compared and from this an actual rotation angle is determined.

A further feature or aspect of an embodiment is believed at the time of the filing of this patent application to possibly reside broadly in the method, wherein the actual determined rotation angle is used to monitor the rotation angle and compared with the predefined angle and its tolerances, wherein a deviation outside the tolerances is detected as a fault.

Another feature or aspect of an embodiment is believed at the time of the filing of this patent application to possibly reside broadly in the method, wherein a position is indicated by giving an angular position and a height position.

Yet another feature or aspect of an embodiment is believed at the time of the filing of this patent application to possibly reside broadly in the method, wherein different illumination units are provided in the detection module, which are selected according to the type of the feature to be detected.

One feature or aspect of an embodiment is believed at the time of the filing of this patent application to possibly reside broadly in an apparatus for fault inspection of at least one container with detection of a position of at least one feature arranged on the surface of the container, wherein the apparatus comprises at least one first detection module 1 which is designed to scan optically and/or by sensors, when the container passes through the detection module 1, a predefined position of the feature to be detected in order to detect an actual position of the feature, to determine the actual position and provide this as a data set, at least one first inspection unit 6 which is designed to generate, before performance of an inspection of the container, a mask for the provided position of the feature so that no misdetection occurs in the region of the mask on performance of an inspection, at least one rotary module 8 which is designed to rotate the container by a predefined angle after performance of a first inspection, wherein the position of the feature is calculated with the offset generated by the rotation and provided as a new position for performance of the second inspection, wherein at least one control unit X is provided for passing on the movement-dependent feature position and feature dimension relative to the inspection unit 6 and for corresponding dynamic adaptation of the masks in the inspection region.

Another feature or aspect of an embodiment is believed at the time of the filing of this patent application to possibly reside broadly in the apparatus, wherein the rotary module 8 and the first inspection unit 6 are integrated in the container inspector 9.

Still another feature or aspect of an embodiment is believed at the time of the filing of this patent application to possibly reside broadly in the apparatus which comprises a second inspection unit 7, wherein the first detection module 1, the first inspection unit 6, the rotary module 8 and the second inspection unit 7 are arranged successively in series so that the first inspection is carried out in the first inspection unit 6 and the second inspection in the second inspection unit 7.

A further feature or aspect of an embodiment is believed at the time of the filing of this patent application to possibly reside broadly in the apparatus, which has a second detection module 11 arranged between the rotary module 8 and the second inspection unit 7.

One feature or aspect of an embodiment is believed at the time of the filing of this patent application to possibly reside broadly in a method of inspecting containers or bottles, such as containers or bottles made of glass, PET, or another transparent material, said method comprising the steps of: moving a container into a detection arrangement; detecting an actual position on said container of a container design feature that forms an integral part of said container; determining, using a control arrangement, an exclusion zone comprising said container design feature and a portion of said container surrounding said container design feature; moving said container to a first inspection arrangement; performing a first inspection for undesired characteristics of said container in a portion of said container outside said exclusion zone; rotating said container to permit inspection from a different angle to permit detection of undetected undesired characteristics; moving said container to a second inspection arrangement; and performing a second inspection for undesired characteristics of said container in a portion of said container outside said exclusion zone, which said exclusion zone is in a new position due to the rotation of said container.

Another feature or aspect of an embodiment is believed at the time of the filing of this patent application to possibly reside broadly in the method, wherein said container design feature comprises at least one of: an embossing, a seam, a decoration, an impression, or similar structure or feature.

Yet another feature or aspect of an embodiment is believed at the time of the filing of this patent application to possibly reside broadly in the method, wherein each of said steps of performing a first inspection and performing a second inspection comprises: obtaining image and/or sensor data regarding characteristics of said container; and evaluating only image and/or sensor data for said portion of said container outside of said exclusion zone to prevent evaluation of said container design feature as being an undesired characteristic of said container.

Still another feature or aspect of an embodiment is believed at the time of the filing of this patent application to possibly reside broadly in the method, wherein said method further comprises calculating said new position of said exclusion zone based on said rotation of said container.

A further feature or aspect of an embodiment is believed at the time of the filing of this patent application to possibly reside broadly in the method, wherein said step of performing a second inspection comprises evaluating said container design feature as being an undesired characteristic of said container, upon an erroneous rotation of said container and said container design feature thereby being positioned outside of the calculated, new position of said exclusion zone.

Another feature or aspect of an embodiment is believed at the time of the filing of this patent application to possibly reside broadly in the method, wherein: said step of rotating said container comprises rotating said container one of: about 90°, essentially 90°, or 90°; and said step of detecting said container design feature comprises scanning optically and/or by sensors with a 360° coverage.

Yet another feature or aspect of an embodiment is believed at the time of the filing of this patent application to possibly reside broadly in the method, wherein: said first inspection arrangement and second inspection arrangement are disposed in a housing; said step of performing a first inspection comprises inspecting a side wall of said container at an inlet of said housing; said step of performing a second inspection comprises inspecting a side wall of said container at an outlet of said housing; and said step of rotating said container comprises rotating said container using a belt drive disposed in said housing between said first inspection arrangement and second inspection arrangement.

Still another feature or aspect of an embodiment is believed at the time of the filing of this patent application to possibly reside broadly in the method, wherein: said step of detecting an actual position of said container design feature comprises detecting an angular position with respect to a rotational axis of said container, and a height position with respect to a bottom of said container; and said detection arrangement comprises one or more types of illumination units, each being configured to detect a specific type of container characteristic.

A further feature or aspect of an embodiment is believed at the time of the filing of this patent application to possibly reside broadly in the method, wherein said method further comprises: detecting an actual position on said container of said container design feature after said container has been rotated and before said step of performing a second inspection; and determining said new position of said exclusion zone based on the actual position of said container design feature.

Another feature or aspect of an embodiment is believed at the time of the filing of this patent application to possibly reside broadly in the method, wherein said method further comprises determining the actual angle of rotation of said container by comparing the detected actual positions of said container design feature before and after rotation of said container.

Yet another feature or aspect of an embodiment is believed at the time of the filing of this patent application to possibly reside broadly in the method, wherein said method further comprises monitoring rotation of said container and subsequent containers by comparing the actual angle of rotation of each container with a predetermined angle of rotation, and detecting an error upon the actual angle of rotation being outside of the tolerance of the predetermined angle of rotation.

Still another feature or aspect of an embodiment is believed at the time of the filing of this patent application to possibly reside broadly in the method, wherein: said step of rotating said container comprises rotating said container one of: about 90°, essentially 90°, or 90°; and said step of detecting said container design feature comprises scanning optically and/or by sensors with a 360° coverage.

A further feature or aspect of an embodiment is believed at the time of the filing of this patent application to possibly reside broadly in the method, wherein: said first inspection arrangement and second inspection arrangement are disposed in a housing; said step of performing a first inspection comprises inspecting a side wall of said container at an inlet of said housing; said step of performing a second inspection comprises inspecting a side wall of said container at an outlet of said housing; and said step of rotating said container comprises rotating said container using a belt drive disposed in said housing between said first inspection arrangement and second inspection arrangement.

One feature or aspect of an embodiment is believed at the time of the filing of this patent application to possibly reside broadly in the method, wherein: said step of detecting an actual position of said container design feature comprises detecting an angular position with respect to a rotational axis of said container, and a height position with respect to a bottom of said container; and said detection arrangement comprises one or more types of illumination units, each being configured to detect a specific type of container characteristic.

One feature or aspect of an embodiment is believed at the time of the filing of this patent application to possibly reside broadly in a container inspection machine for inspecting containers or bottles, such as containers or bottles made of glass, PET, or another transparent material, said container inspection machine comprising: a moving arrangement configured to move containers through said container inspection machine; a detection arrangement configured to detect an actual position on said container of a container design feature that forms an integral part of said container; a control arrangement configured to determine an exclusion zone comprising said container design feature and a portion of said container surrounding said container design feature; a first inspection arrangement configured to perform a first inspection for undesired characteristics of said container in a portion of said container outside said exclusion zone; a rotation arrangement configured to rotate said container to permit inspection from a different angle to permit detection of undetected undesired characteristics; and a second inspection arrangement configured to perform a second inspection for undesired characteristics of said container in a portion of said container outside said exclusion zone, which said exclusion zone is in a new position due to the rotation of said container.

Another feature or aspect of an embodiment is believed at the time of the filing of this patent application to possibly reside broadly in the container inspection machine, wherein said detection arrangement is configured to detect a container design feature comprising at least one of: an embossing, a seam, a decoration, an impression, or similar structure or feature.

Yet another feature or aspect of an embodiment is believed at the time of the filing of this patent application to possibly reside broadly in the container inspection machine, wherein said rotation arrangement, first inspection arrangement, and said second inspection arrangement are disposed in a housing.

Still another feature or aspect of an embodiment is believed at the time of the filing of this patent application to possibly reside broadly in the container inspection machine, wherein said moving arrangement is configured to move containers to said detection arrangement, then to said first inspection arrangement, then to said rotation arrangement, and then to said second inspection arrangement, along a path of movement of the containers.

A further feature or aspect of an embodiment is believed at the time of the filing of this patent application to possibly reside broadly in the container inspection machine, wherein: said container inspection machine further comprises a second detection arrangement configured to detect an actual position on said container of a container design feature that forms an integral part of said container; said second detection arrangement is disposed between said rotation arrangement and said second inspection arrangement, along said path of movement of the containers; and said control arrangement is configured to determine a new position of said exclusion zone based on the actual position of said container design feature detected by said second detection arrangement.

Another feature or aspect of an embodiment is believed at the time of the filing of this patent application to possibly reside broadly in the container inspection machine, wherein: each of said first and second inspection arrangements comprises optical detection devices and/or electronic sensors configured to obtain image and/or sensor data regarding characteristics of said container; and said control arrangement is configured to evaluate only image and/or sensor data for said portion of said container outside of said exclusion zone to prevent evaluation of said container design feature as being an undesired characteristic of said container.

The present application relates to a method for inspecting at least one container, as a rule bottles 5, by detecting a position of a feature arranged on a surface of the container, in which the container or the bottle, before inspection, runs through a detection module 1, in which a predefined position of the feature to be detected is scanned optically and/or by sensors in order to detect an actual position of the feature, and the actual position is determined; during a subsequent first inspection 6 a first mask is generated for the determined position of the feature, such that, when performing the first inspection 6 no misdetection occurs in the area of the first mask; after the first inspection has been performed, the container is rotated by a predefined angle (using a rotary module 8), then the position of the feature is offset with the offset generated by the rotation and is provided as a new position during the performance of a second inspection 7; during the second inspection, a second mask is generated for the provided new position of the feature, such that when the second inspection is performed in the area of the second mask, no misdetection occurs.

The components disclosed in the patents, patent applications, patent publications, and other documents disclosed or incorporated by reference herein, may possibly be used in possible embodiments of the present invention, as well as equivalents thereof.

The purpose of the statements about the technical field is generally to enable the Patent and Trademark Office and the public to determine quickly, from a cursory inspection, the nature of this patent application. The description of the technical field is believed, at the time of the filing of this patent application, to adequately describe the technical field of this patent application. However, the description of the technical field may not be completely applicable to the claims as originally filed in this patent application, as amended during prosecution of this patent application, and as ultimately allowed in any patent issuing from this patent application. Therefore, any statements made relating to the technical field are not intended to limit the claims in any manner and should not be interpreted as limiting the claims in any manner.

The appended drawings in their entirety, including all dimensions, proportions and/or shapes in at least one embodiment of the invention, are accurate and are hereby included by reference into this specification.

The background information is believed, at the time of the filing of this patent application, to adequately provide background information for this patent application. However, the background information may not be completely applicable to the claims as originally filed in this patent application, as amended during prosecution of this patent application, and as ultimately allowed in any patent issuing from this patent application. Therefore, any statements made relating to the background information are not intended to limit the claims in any manner and should not be interpreted as limiting the claims in any manner.

All, or substantially all, of the components and methods of the various embodiments may be used with at least one embodiment or all of the embodiments, if more than one embodiment is described herein.

The purpose of the statements about the object or objects is generally to enable the Patent and Trademark Office and the public to determine quickly, from a cursory inspection, the nature of this patent application. The description of the object or objects is believed, at the time of the filing of this patent application, to adequately describe the object or objects of this patent application. However, the description of the object or objects may not be completely applicable to the claims as originally filed in this patent application, as amended during prosecution of this patent application, and as ultimately allowed in any patent issuing from this patent application. Therefore, any statements made relating to the object or objects are not intended to limit the claims in any manner and should not be interpreted as limiting the claims in any manner.

All of the patents, patent applications, patent publications, and other documents cited herein, and in the Declaration attached hereto, are hereby incorporated by reference as if set forth in their entirety herein except for the exceptions indicated herein.

The summary is believed, at the time of the filing of this patent application, to adequately summarize this patent application. However, portions or all of the information contained in the summary may not be completely applicable to the claims as originally filed in this patent application, as amended during prosecution of this patent application, and as ultimately allowed in any patent issuing from this patent application. Therefore, any statements made relating to the summary are not intended to limit the claims in any manner and should not be interpreted as limiting the claims in any manner.

It will be understood that the examples of patents, patent applications, patent publications, and other documents which are included in this application and which are referred to in paragraphs which state "Some examples of . . . which may possibly be used in at least one possible embodiment of the present application . . . " may possibly not be used or useable in any one or more embodiments of the application.

The sentence immediately above relates to patents, patent applications, patent publications, and other documents either incorporated by reference or not incorporated by reference.

All of the patents, patent applications, patent publications, and other documents, except for the exceptions indicated herein, which were cited in the International Search Report dated Aug. 8, 2013, and/or cited elsewhere, as well as the International Search Report document itself, are hereby incorporated by reference as if set forth in their entirety herein except for the exceptions indicated herein, as follows: DE 3611536, having the title "Device for automatically testing transparent objects, in particular glass bottles", published on Apr. 5, 1986; and U.S. Pat. No. 5,729,340, having the title "Bottle inspection machine", published on Jul. 30, 1997.

All of the patents, patent applications, patent publications, and other documents, except for the exceptions indicated herein, which were cited in the German Office Action dated Dec. 20, 2012, and/or cited elsewhere, as well as the German Office Action document itself, are hereby incorporated by reference as if set forth in their entirety herein except for the exceptions indicated herein, as follows: DE 10 2008 053 876, having the title "Flaschennaht- und Embossingausrichtung", published on May 6, 2010; DE 10 2010 032 166, having the title "Erfassungssystem und Inspektionsverfahren zur Flaschennaht- und Embossingausrichtung", published on Jan. 26, 2012; and EP 1 628 241, having the title "Device for detecting structures, such as profiles or stampings, on bodies of bottles or similar containers", published on Feb. 22, 2006.

The corresponding foreign and international patent publication applications, namely, Federal Republic of Germany Patent Application No. 10 2012 009 783, filed on May 18, 2012, having inventors Jürgen HERRMANN, Wolfgang SCHORN, Marius Michael HERRMANN, and Xiang ZHANG, and DE-OS 10 2012 009 783 and DE-PS 10 2012 009 783, and International Application No. PCT/2013/

001092, filed on Apr. 13, 2013, having WIPO Publication No. WO2013/170920 and inventors Jürgen HERRMANN, Wolfgang SCHORN, Marius Michael HERRMANN, and Xiang ZHANG, are hereby incorporated by reference as if set forth in their entirety herein, except for the exceptions indicated herein, for the purpose of correcting and explaining any possible misinterpretations of the English translation thereof. In addition, the published equivalents of the above corresponding foreign and international patent publication applications, and other equivalents or corresponding applications, if any, in corresponding cases in the Federal Republic of Germany and elsewhere, and the references and documents cited in any of the documents cited herein, such as the patents, patent applications, patent publications, and other documents, except for the exceptions indicated herein, are hereby incorporated by reference as if set forth in their entirety herein except for the exceptions indicated herein.

The purpose of incorporating the corresponding foreign equivalent patent application(s), that is, PCT/2013/001092 and German Patent Application 10 2012 009 783, is solely for the purposes of providing a basis of correction of any wording in the pages of the present application, which may have been mistranslated or misinterpreted by the translator, and to provide additional information relating to technical features of one or more embodiments, which information may not be completely disclosed in the wording in the pages of this application.

Statements made in the original foreign patent applications PCT/2013/001092 and DE 10 2012 009 783 from which this patent application claims priority which do not have to do with the correction of the translation in this patent application are not to be included in this patent application in the incorporation by reference.

Any statements about admissions of prior art in the original foreign patent applications PCT/2013/001092 and DE 10 2012 009 783 are not to be included in this patent application in the incorporation by reference, since the laws relating to prior art in non-U.S. Patent Offices and courts may be substantially different from the Patent Laws of the United States.

All of the references and documents cited in any of the patents, patent applications, patent publications, and other documents cited herein, except for the exceptions indicated herein, are hereby incorporated by reference as if set forth in their entirety herein except for the exceptions indicated herein. All of the patents, patent applications, patent publications, and other documents cited herein, referred to in the immediately preceding sentence, include all of the patents, patent applications, patent publications, and other documents cited anywhere in the present application.

Words relating to the opinions and judgments of the author of all patents, patent applications, patent publications, and other documents cited herein and not directly relating to the technical details of the description of the embodiments therein are not incorporated by reference.

The words all, always, absolutely, consistently, preferably, guarantee, particularly, constantly, ensure, necessarily, immediately, endlessly, avoid, exactly, continually, expediently, ideal, need, must, only, perpetual, precise, perfect, require, requisite, simultaneous, total, unavoidable, and unnecessary, or words substantially equivalent to the above-mentioned words in this sentence, when not used to describe technical features of one or more embodiments of the patents, patent applications, patent publications, and other documents, are not considered to be incorporated by reference herein for any of the patents, patent applications, patent publications, and other documents cited herein.

The description of the embodiment or embodiments is believed, at the time of the filing of this patent application, to adequately describe the embodiment or embodiments of this patent application. However, portions of the description of the embodiment or embodiments may not be completely applicable to the claims as originally filed in this patent application, as amended during prosecution of this patent application, and as ultimately allowed in any patent issuing from this patent application. Therefore, any statements made relating to the embodiment or embodiments are not intended to limit the claims in any manner and should not be interpreted as limiting the claims in any manner.

The details in the patents, patent applications, patent publications, and other documents cited herein may be considered to be incorporable, at applicant's option, into the claims during prosecution as further limitations in the claims to patentably distinguish any amended claims from any applied prior art.

The purpose of the title of this patent application is generally to enable the Patent and Trademark Office and the public to determine quickly, from a cursory inspection, the nature of this patent application. The title is believed, at the time of the filing of this patent application, to adequately reflect the general nature of this patent application. However, the title may not be completely applicable to the technical field, the object or objects, the summary, the description of the embodiment or embodiments, and the claims as originally filed in this patent application, as amended during prosecution of this patent application, and as ultimately allowed in any patent issuing from this patent application. Therefore, the title is not intended to limit the claims in any manner and should not be interpreted as limiting the claims in any manner.

The abstract of the disclosure is submitted herewith as required by 37 C.F.R. §1.72(b). As stated in 37 C.F.R. §1.72(b):

A brief abstract of the technical disclosure in the specification must commence on a separate sheet, preferably following the claims, under the heading "Abstract of the Disclosure." The purpose of the abstract is to enable the Patent and Trademark Office and the public generally to determine quickly from a cursory inspection the nature and gist of the technical disclosure. The abstract shall not be used for interpreting the scope of the claims.

Therefore, any statements made relating to the abstract are not intended to limit the claims in any manner and should not be interpreted as limiting the claims in any manner.

The embodiments of the invention described herein above in the context of the preferred embodiments are not to be taken as limiting the embodiments of the invention to all of the provided details thereof, since modifications and variations thereof may be made without departing from the spirit and scope of the embodiments of the invention.

What is claimed is:

1. A method of inspecting containers, said method comprising the steps of:

moving a container into a detection arrangement;

detecting an actual position on said container of a container design feature that forms an integral part of said container;

determining, using a control arrangement, an exclusion zone comprising said container design feature and a portion of said container surrounding said container design feature;

moving said container to a first inspection arrangement;

performing a first inspection for undesired characteristics of said container in a portion of said container outside said exclusion zone;

rotating said container to permit inspection from a different angle to permit detection of undetected undesired characteristics;

moving said container to a second inspection arrangement; and performing a second inspection for undesired characteristics of said container in a portion of said container outside said exclusion zone, which said exclusion zone is in a new position due to the rotation of said container.

2. The method according to claim 1, wherein said container design feature comprises at least one of: an embossing, a seam, a decoration, an impression, or similar structure or feature.

3. The method according to claim 2, wherein each of said steps of performing a first inspection and performing a second inspection comprises:

obtaining image data regarding characteristics of said container; and evaluating only image data for said portion of said container outside of said exclusion zone to prevent evaluation of said container design feature as being an undesired characteristic of said container.

4. The method according to claim 3, wherein said method further comprises calculating said new position of said exclusion zone based on said rotation of said container.

5. The method according to claim 4, wherein said step of performing a second inspection comprises evaluating said container design feature as being an undesired characteristic of said container, upon an erroneous rotation of said container and said container design feature thereby being positioned outside of the calculated, new position of said exclusion zone.

6. The method according to claim 5, wherein:

said step of rotating said container comprises rotating said container one of: about 90°, essentially 90°, or 90°; and said step of detecting said container design feature comprises scanning optically or by sensors with a 360° coverage.

7. The method according to claim 6, wherein:

said first inspection arrangement and second inspection arrangement are disposed in a housing;

said step of performing a first inspection comprises inspecting a side wall of said container at an inlet of said housing;

said step of performing a second inspection comprises inspecting a side wall of said container at an outlet of said housing; and said step of rotating said container comprises rotating said container using a belt drive disposed in said housing between said first inspection arrangement and second inspection arrangement.

8. The method according to claim 7, wherein:

said step of detecting an actual position of said container design feature comprises detecting an angular position with respect to a rotational axis of said container, and a height position with respect to a bottom of said container;

said detection arrangement comprises one or more types of illumination units, each being configured to detect a specific type of container characteristic; and said containers comprise empty containers or bottles made of glass, PET, or other transparent or translucent material.

9. The method according to claim 3, wherein said method further comprises:

detecting an actual position on said container of said container design feature after said container has been rotated and before said step of performing a second inspection; and determining said new position of said exclusion zone based on the actual position of said container design feature.

10. The method according to claim 9, wherein said method further comprises determining the actual angle of rotation of said container by comparing the detected actual positions of said container design feature before and after rotation of said container.

11. The method according to claim 10, wherein:

said method further comprises monitoring rotation of said container and subsequent containers by comparing the actual angle of rotation of each container with a predetermined angle of rotation, and detecting an error upon the actual angle of rotation being outside of the tolerance of the predetermined angle of rotation; and said containers comprise empty containers or bottles made of glass, PET, or other transparent or translucent material.

12. The method according to claim 9, wherein:

said step of rotating said container comprises rotating said container one of: about 90°, essentially 90°, or 90°; and said step of detecting said container design feature comprises scanning optically or by sensors with a 360° coverage.

13. The method according to claim 12, wherein:

said first inspection arrangement and second inspection arrangement are disposed in a housing;

said step of performing a first inspection comprises inspecting a side wall of said container at an inlet of said housing;

said step of performing a second inspection comprises inspecting a side wall of said container at an outlet of said housing; and said step of rotating said container comprises rotating said container using a belt drive disposed in said housing between said first inspection arrangement and second inspection arrangement.

14. The method according to claim 13, wherein:

said step of detecting an actual position of said container design feature comprises detecting an angular position with respect to a rotational axis of said container, and a height position with respect to a bottom of said container;

said detection arrangement comprises one or more types of illumination units, each being configured to detect a specific type of container characteristic; and said containers comprise empty containers or bottles made of glass, PET, or other transparent or translucent material.

15. A container inspection machine for inspecting containers, said container inspection machine comprising:

a conveyor to move containers through said container inspection machine;

a detection module comprising optical scanners or sensor scanners to detect an actual position on said container of a container design feature that forms an integral part of said container;

a control computer to determine an exclusion zone comprising said container design feature and a portion of said container surrounding said container design feature;

a first inspection unit comprising an image recorder to perform a first inspection for undesired characteristics of said container in a portion of said container outside said exclusion zone;

a container rotator to rotate said container to permit inspection from a different angle to permit detection of undetected undesired characteristics; and a second inspection unit comprising an image recorder to perform a second inspection for undesired characteristics of said container in a portion of said container outside said exclusion zone, which said exclusion zone is in a new position due to the rotation of said container.

16. The container inspection machine according to claim 15, wherein said optical scanners or said sensor scanners are positioned to detect a container design feature comprising at least one of: an embossing, a seam, a decoration, an impression, or similar structure or feature.

17. The container inspection machine according to claim 15, wherein said container rotator, said first inspection unit and said second inspection unit are disposed in a housing.

18. The container inspection machine according to claim 17, wherein said conveyor is positioned to move containers to said detection module, then to said first inspection unit, then to said container rotator, and then to said second inspection unit along a path of movement of the containers.

19. The container inspection machine according to claim 18, wherein:

said container inspection machine further comprises a second detection module;

said second detection module comprises optical scanners or sensor scanners to detect an actual position on said container of a container design feature that forms an integral part of said container;

said second detection module is disposed between said container rotator and said second inspection module, along said path of movement of the containers; and said control computer is configured to determine a new position of said exclusion zone based on the actual position of said container design feature detected by said second detection module.

20. The container inspection machine according to claim 19, wherein said control computer is configured to evaluate only image data for said portion of said container outside of said exclusion zone to prevent evaluation of said container design feature as being an undesired characteristic of said container.

* * * * *